US012721824B2

(12) United States Patent
Chen et al.

(10) Patent No.: US 12,721,824 B2
(45) **Date of Patent: *Sep. 1, 2026**

(54) COMPOSITION FOR INHIBITING PARKINSON'S DISEASE AND METHOD OF MANUFACTURING THE SAME

(71) Applicant: Forte Capital Ltd., Taipei City (TW)

(72) Inventors: Bing-Huei Chen, Taipei City (TW); Yi-Chun Wang, Taipei City (TW); Yung-Sheng Chang, Taipei City (TW); Tai-Yi He, Taipei City (TW)

(73) Assignee: Forte Capital Ltd., Taipei (TW)

( * ) Notice: Subject to any disclaimer, the term of this patent is extended or adjusted under 35 U.S.C. 154(b) by 465 days.

This patent is subject to a terminal disclaimer.

(21) Appl. No.: 18/359,675

(22) Filed: Jul. 26, 2023

(65) Prior Publication Data

US 2024/0033231 A1 Feb. 1, 2024

(30) Foreign Application Priority Data

Jul. 26, 2022 (TW) ................................. 111128027
Dec. 7, 2022 (TW) ................................. 111147050

(51) Int. Cl.

| | |
|---|---|
| ***A61K 31/11*** | (2006.01) |
| ***A61K 9/107*** | (2006.01) |
| ***A61K 31/045*** | (2006.01) |
| ***A61K 31/085*** | (2006.01) |
| ***A61K 31/192*** | (2006.01) |
| ***A61K 31/352*** | (2006.01) |
| ***A61K 31/37*** | (2006.01) |

(Continued)

(52) U.S. Cl.

CPC ............ *A61K 31/11* (2013.01); *A61K 9/1075* (2013.01); *A61K 31/045* (2013.01); *A61K 31/085* (2013.01); *A61K 31/192* (2013.01); *A61K 31/352* (2013.01); *A61K 31/37* (2013.01); *A61K 31/7028* (2013.01); *A61K 31/7048* (2013.01); *A61K 36/54* (2013.01); *A61K 47/24* (2013.01); *A61K 47/44* (2013.01); *A61P 25/16* (2018.01)

(58) Field of Classification Search

CPC .... A61K 31/045; A61K 31/085; A61K 31/11; A61K 31/192; A61K 31/352; A61K 31/37; A61K 31/7028; A61K 31/7048; A61K 36/54; A61K 47/24; A61K 47/44; A61K 9/1075; A61P 25/16

See application file for complete search history.

(56) References Cited

FOREIGN PATENT DOCUMENTS

| | | | |
|---|---|---|---|
| CN | 102302449 | * | 1/2012 |
| KR | 20100058032 | * | 7/2011 |

OTHER PUBLICATIONS

Ouyang et al CN 102302449- English translation (Year: 2011).*

(Continued)

*Primary Examiner* — Savitha M Rao

(74) *Attorney, Agent, or Firm* — MUNCY, GEISSLER, OLDS & LOWE, P.C.

(57) ABSTRACT

A composition for inhibiting Parkinson's disease is provided, comprising 1 part by weight of soybean oil, 5 to 14 parts by weight of an emulsifier, 0.5 to 2 parts by weight of lecithin, 81 to 91 parts by weight of deionized water, and 2.345 to 17.833 parts by weight of cinnamaldehyde. Furthermore, the present invention also provides a method for manufacturing the composition for inhibiting Parkinson's disease, to produce the aforementioned composition for inhibiting Parkinson's disease.

15 Claims, 1 Drawing Sheet

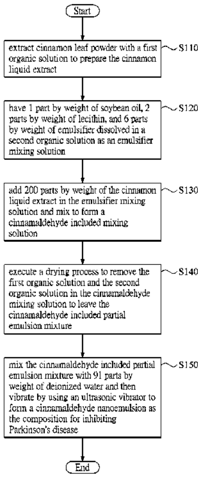

(51) Int. Cl.

| | |
|---|---|
| ***A61K 31/7028*** | (2006.01) |
| ***A61K 31/7048*** | (2006.01) |
| ***A61K 36/54*** | (2006.01) |
| ***A61K 47/24*** | (2006.01) |
| ***A61K 47/44*** | (2017.01) |
| ***A61P 25/16*** | (2006.01) |

(56) References Cited

OTHER PUBLICATIONS

Lee (KR 20100058032A English translation (Year: 2010).*
Huang et al. (Industrial crops and products 162, 2021 , pp. 1-9) (Year: 2021).*

* cited by examiner

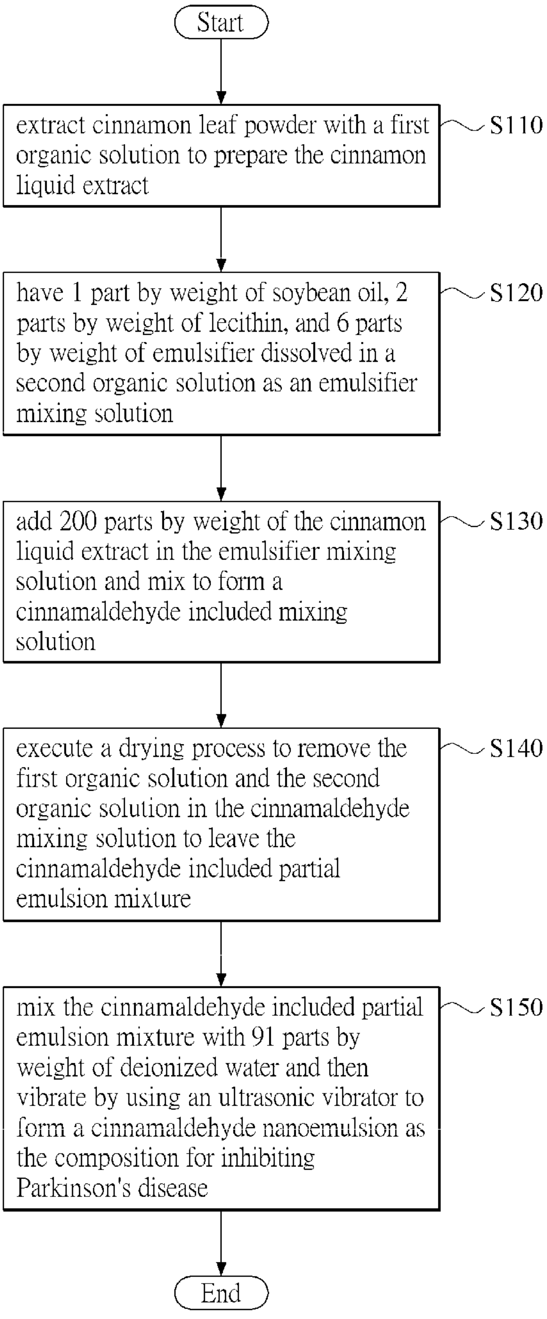
Start
extract cinnamon leaf powder with a first organic solution to prepare the cinnamon liquid extract
S110
have 1 part by weight of soybean oil, 2 parts by weight of lecithin, and 6 parts by weight of emulsifier dissolved in a second organic solution as an emulsifier mixing solution
S120
add 200 parts by weight of the cinnamon liquid extract in the emulsifier mixing solution and mix to form a cinnamaldehyde included mixing solution
S130
execute a drying process to remove the first organic solution and the second organic solution in the cinnamaldehyde mixing solution to leave the cinnamaldehyde included partial emulsion mixture
S140
mix the cinnamaldehyde included partial emulsion mixture with 91 parts by weight of deionized water and then vibrate by using an ultrasonic vibrator to form a cinnamaldehyde nanoemulsion as the composition for inhibiting Parkinson's disease
S150
End

COMPOSITION FOR INHIBITING PARKINSON'S DISEASE AND METHOD OF MANUFACTURING THE SAME

This application claims the benefit of Taiwan Patent Application Serial No. 111128027, filed Jul. 26, 2022 and Serial No. 111147050, filed Dec. 7, 2022, the subject matter of which is incorporated herein by reference.

BACKGROUND OF THE INVENTION

Field of the Invention

The present invention is related to a composition and a method of manufacturing the same, and more particularly is related to a composition for inhibiting Parkinson's disease and a method of manufacturing the same.

Description of the Related Art

It is well known that Parkinson's disease (PD) is a common neurodegenerative disease. According to the estimation of World Health Organization (WHO), there would be about 18 million individuals with PD, and the number will double every year. For the countries with population ageing, health care will be a huge burden.

PD is a motor disorder disease, mainly caused by degeneration of basal ganglia and substantia nigra in the brain, which leads to a loss of neurotransmitter dopamine. Dopamine is similar to other monoamine neurotransmitters, which slowly adjust the rapid neurotransmission mediated by glutamic acid (GA) and Gamma-aminobutyric acid (GABA), so as to play a role in neuro circuits, especially the Physiological actions important for the aspects of smell modulation, retina modulation, hormone modulation, cardiovascular function, sympathetic nervous system modulation, immune system and Renal function. Substantia nigra is a type of neuron with not respond to any stimulation, which is used for the development and maintenance of brain. When the amount of dopamine produced by substantia nigra is below 80% of that of the normal people, the symptoms of PD exist.

Ageing may also causes decreasing of dopamine, norepinephrine, and serotonin in frontal sinuses of the brain, and size reduction and functional decline of cerebral cortex. Older people may have movement disorders like the patients with frontal lobe syndrome, such as unable to inhibit interference which may cause preservation errors and a decline of working memory ability. Neuroscientists suggest frontal lobe deficiency is the major reason of movement disorders. Frontal lobe white matter of brain is degenerated associated with aging. The degeneration may influence memory circuits of frontal cortex. Such change may be observed in the individuals even without the symptoms of Alzheimer's disease or hypertension.

In addition to insufficiency of dopamine generation, many other reasons are believed to be associated with PD, which includes generation of oxidizing pressure. The free radical generated in human body may react with lipid of cell membranes in brain to generate lipid peroxides, which may cause damage of cell membranes or death of neuron cells.

Moreover, it is found that substantia nigra in the brain of patients with PD has increased iron content and decreased glutathione content. It is proved that the increasing of iron levels can promote the generation of lipid peroxides. Thus, insufficient intake of antioxidants may cause death of dopaminergic neurons.

In the past few years, many natural antioxidants such as Phenolic acid and Flavonoids in plants are believed to provide the benefit of increasing cognitive abilities and protecting brain health. Wherein, it is described that cinnamon is an effective free radical cleaner, cinnamon and its derivative cinnamaldehyde can be used as a strong antioxidant and anti-inflammatory. Cinnamon is metabolized by the liver to generate Sodium Benzoate which may penetrate blood brain barrier. In research, it is found that for the sick mice with PD, after feeding cinnamon powder, Sodium Benzoate transformed from cinnamon may reach the brain to prevent the loss of Parkinson's disease protein and DJ-1 protein so as to protect the neurons effectively and recovery the generation of neurotransmitter to further improve moving abilities of sick mice with PD.

As mentioned above, the present study about PD only suggests that eating cinnamon is helpful for inhibiting PD. But the topic about how to use cinnamon to enhance the effect of inhibiting PD more effectively is still needed to do further research and development.

BRIEF SUMMARY OF THE INVENTION

In view of the prior art, which only suggests that eating cinnamon has certain inhibiting function for PD but fails to optimize the usage of cinnamon effectively. Accordingly, it is a main object of the present invention to provide a composition for inhibiting PD and a manufacturing method thereof, which is capable to produce a composition that makes cinnamaldehyde absorbed more easily through a specific composition ratio and manufacturing method, to better inhibit PD effectively.

In order to resolve the problem of prior art, the disclosure provides a composition for inhibiting Parkinson's disease. The composition for inhibiting Parkinson's disease comprises 1 part by weight of soybean oil, 5 to 14 parts by weight of emulsifier, 0.5 to 2 parts by weight of lecithin, 81 to 91 parts by weight of deionized water, and 2.345 to 17.833 parts by weight of cinnamaldehyde, wherein an average particle size of the composition for inhibiting Parkinson's disease is 30 nm, and a polydispersity index of the composition for inhibiting Parkinson's disease is ranged between 0.14 to 0.18.

In accordance with an embodiment of the present disclosure, the composition for inhibiting Parkinson's disease further comprises 0.14734 to 0.8813 parts by weight of cinnamic acid.

In accordance with an embodiment of the present disclosure, the composition for inhibiting Parkinson's disease further comprises 0.04122 to 0.4334 parts by weight of cinnamyl alcohol.

In accordance with an embodiment of the present disclosure, the composition for inhibiting Parkinson's disease further comprises 0.02504 to 0.0833 parts by weight of kaempferol.

In accordance with an embodiment of the present disclosure, the composition for inhibiting Parkinson's disease further comprises 0.0177 to 0.0947 parts by weight of benzoic acid.

In accordance with an embodiment of the present disclosure, the composition for inhibiting Parkinson's disease further comprises 0.0102 to 0.156 parts by weight of eugenol In accordance with an embodiment of the present disclosure, the composition for inhibiting Parkinson's disease further comprises 0.0037 to 0.0093 parts by weight of quercetin.

In accordance with an embodiment of the present disclosure, the composition for inhibiting Parkinson's disease further comprises 0.02504 to 0.0833 parts by weight of kaempferol-3-β-D-glucopyranoside.

In accordance with an embodiment of the present disclosure, the composition for inhibiting Parkinson's disease further comprises 0.0011 to 0.0067 parts by weight of rutin.

In accordance with an embodiment of the present disclosure, the composition for inhibiting Parkinson's disease further comprises 0.00108 to 0.00521 parts by weight of caffeic acid, 0.00086 to 0.0012 parts by weight of coumarin, 0.00038 to parts by weight of hyperoside and isoquercetin, 0.00080 to 0.001 parts by weight of p-coumaric acid, and 0.00012 to 0.0015 parts by weight of neochlorogenic acid.

In addition, a method of manufacturing the composition for inhibiting Parkinson's disease as mentioned above is also provided. The method comprises the following steps (A) to (E).

Firstly, step (A) is to prepare a cinnamon liquid extract, wherein the cinnamon liquid extract comprises a first organic solution and at least one solute totally dissolved in the first organic solution, wherein the at least one solute comprises 90% to 99% by weight of cinnamaldehyde.

Then, step (B) is to have 1 part by weight of soybean oil, 2 parts by weight of lecithin, and 6 parts by weight of emulsifier dissolved in a second organic solution as an emulsifier mixing solution, wherein the first organic solution and the second organic solution are ethanol solutions.

Thereafter, step (C) is to add 200 parts by weight of the cinnamon liquid extract in the emulsifier mixing solution and mixing to form a cinnamaldehyde included mixing solution, wherein the cinnamaldehyde included mixing solution comprises the first organic solution and the second organic solution, wherein the cinnamaldehyde, the soybean oil, and the lecithin in the cinnamaldehyde add mixing solution are miscible with each other to form a cinnamaldehyde included oil, and the cinnamaldehyde included oil and the emulsifier are partially bonded to form a cinnamaldehyde included partial emulsion mixture.

Then, step (D) is to execute a drying process to remove the first organic solution and the second organic solution in the cinnamaldehyde mixing solution to leave the cinnamaldehyde included partial emulsion mixture.

Finally, step (E) is to mix the cinnamaldehyde included partial emulsion mixture with 91 parts by weight of deionized water to form a cinnamaldehyde nanoemulsion as the composition for inhibiting Parkinson's disease.

In accordance with an embodiment of the present disclosure, the step (E) is to mix the cinnamaldehyde included partial emulsion mixture with 91 parts by weight of the deionized water and then vibrate by using an ultrasonic vibrator to form the cinnamaldehyde nanoemulsion.

In accordance with an embodiment of the present disclosure, a concentration of the ethanol solution is higher than 80%.

In accordance with an embodiment of the present disclosure, the step (A) is to extract cinnamon leaf powder with the first organic solution to prepare the cinnamon liquid extract. Preferably, a weight ratio of the cinnamon leaf powder and the first organic solution is 1:5.

As described, it is proved though experiments that cinnamaldehyde nanoemulsion produced by the present invention is more effective for inhibiting Parkinson's disease than the existed cinnamon liquid extract or Indigenous cinnamon hydrosol, and thus can be used as the composition for inhibiting Parkinson's disease.

Further features of the present invention would be described in the following embodiments and FIGURE.

BRIEF DESCRIPTION OF THE DRAWINGS

The sole FIGURE is a flow chart showing the method of manufacturing a composition for inhibiting Parkinson's disease in accordance with a preferred embodiment of the present invention.

DETAILED DESCRIPTION OF THE EMBODIMENTS

Specific implementations of this disclosure are further described in detail below with reference to the accompanying drawings. According to the following descriptions and claims, the advantages and features of this disclosure are clearer. It should be noted that the drawings are drawn by using an extremely simplified form and imprecise proportion, which are only used for conveniently and clearly assisting in explaining the objective of the embodiments of this disclosure.

In accordance with a preferred embodiment of the present invention, a composition for inhibiting Parkinson's disease which mainly contains soybean oil, emulsifier, lecithin, deionized water and cinnamaldehyde is provided. The composition for inhibiting Parkinson's disease provided in the present embodiment is to produce cinnamaldehyde nano particles by using soybean oil, emulsifier, lecithin and deionized water to improve body absorption so as to enhance efficacy of cinnamaldehyde for inhibiting Parkinson's disease.

Please refer to the sole FIGURE, wherein the sole FIGURE is a flow chart showing the method of manufacturing a composition for inhibiting Parkinson's disease in accordance with a preferred embodiment of the present invention. As shown, the method of manufacturing the composition for inhibiting Parkinson's disease comprises the following steps S110 to S150.

Firstly, step S110 is to extract cinnamon leaf powder with a first organic solution to prepare the cinnamon liquid extract, wherein, a weight ratio of the cinnamon leaf powder and the first organic solution is 1:5 for example. The cinnamon liquid extract comprises a first organic solution and at least one solute totally dissolved in the first organic solution.

In the present embodiment, the first organic solution is an ethanol solution with a concentration higher than 80%, and the solute comprises 90 wt % to 99 wt % of cinnamaldehyde. However, the present invention is not restricted thereto. The other organic solutions capable of extracting cinnamaldehyde can be used as the first organic solution.

As mentioned above, the solute is the substance of the ingredients of the cinnamon leaf powder capable to be extracted by the first organic solution. The percentage of cinnamaldehyde contained in the solute mainly depends on the factors such as growing conditions and species of the cinnamon leaf powder. However, the present invention is not restricted thereto. In addition to cinnamaldehyde, the solute may contain other substances such as cinnamyl alcohol. In addition, the species of the cinnamon leaf powder can be Indigenous cinnamon, Cinnamomum zeylanicum, or Cinnamomum cassia, etc.

Then, step S120 is to have 1 part by weight of soybean oil, 2 parts by weight of lecithin, and 6 parts by weight of emulsifier dissolved in a second organic solution as an emulsifier mixing solution, wherein the emulsifier can be Tween 80 (CAS No. 9005-65-6) for example, but the present invention is not restricted thereto, the other emulsifiers commonly used in food industry can be used. In addition, in the present embodiment, the second organic solution is also an ethanol solution, and a concentration of the ethanol solution is higher than 80%.

Afterward, step S130 is to add 200 parts by weight of the cinnamon liquid extract in the emulsifier mixing solution and mix to form a cinnamaldehyde included mixing solution. Because the solvent of the cinnamon liquid extract is the first organic solution and the solvent of the emulsifier mixing solution is the second solution, the cinnamaldehyde included mixing solution comprises the first organic solution and the second organic solution.

In the aforementioned cinnamaldehyde included mixing solution, cinnamaldehyde, soybean oil, and lecithin are miscible with each other to form a cinnamaldehyde included oil, and the cinnamaldehyde included oil and the emulsifier are partially bonded to form a cinnamaldehyde included partial emulsion mixture.

Thereafter, step S140 is to execute a drying process to remove the first organic solution and the second organic solution in the cinnamaldehyde mixing solution to leave the cinnamaldehyde included partial emulsion mixture. For example, the drying process is carried out by reducing pressure to lower the boiling point of the first organic solution and the second organic solution, so as to accelerate the volatilization of the first organic solution and the second organic solution to leave the cinnamaldehyde included partial emulsion mixture. Moreover, in the drying process, other than the way of reducing pressure, nitrogen gas can be used for blowing to the remained first organic solution and the second organic solution after most of the first organic solution and the second organic solution are volatilized, so as to make sure that the first organic solution and the second organic solution are totally volatilized to leave the cinnamaldehyde included partial emulsion mixture.

Finally, step S150 is to mix the cinnamaldehyde included partial emulsion mixture with 91 parts by weight of deionized water and then vibrate by using an ultrasonic vibrator to form a cinnamaldehyde nanoemulsion as the composition for inhibiting Parkinson's disease.

In accordance with the aforementioned method of manufacturing the composition for inhibiting Parkinson's disease, for example, when preparing the cinnamon liquid extract in step S110, if 500 g of cinnamon leaf powder is added in 2500 ml of 80% ethanol solution (the first organic solution), extracted by using ultrasonic vibration at a temperature of 60° C. for 2 hours, and filtered with filter paper in the suction filtration process to collect the supernatant liquid, about 2000 ml of cinnamon liquid extract with 5000 ppm cinnamaldehyde. Thus, it can be found that the cinnamon leaf powder used in the present embodiment contains about 2 wt % of cinnamaldehyde. That is, the cinnamon leaf powder contains about 98 wt % carbohydrate and the other ingredients (including the solutes dissoluble in the first organic solution).

As mentioned above, in step S120, each part by weight can be 0.1 g for example. That is, 0.1 g of soybean oil, 0.2 g of lecithin, and 0.6 g of Tween 80 (the emulsifier) are dissolved in 100 ml of 99% ethanol solution (the second organic solution) to provide the emulsifier mixing solution.

Then, because in the aforementioned step S120, each part by weight is 0.1 g, step S130 is to add 20 g of cinnamon liquid extract in the emulsifier mixing solution and mix to form a cinnamaldehyde included mixing solution, wherein because the cinnamon liquid extract contains 5000 ppm cinnamaldehyde, the density thereof would be slightly increased and close to 1 g/ml. In practice, using 20 g of cinnamon liquid extract in the emulsifier mixing solution is for the purpose of convenience.

Next, because step S140 to execute a drying process to remove the first organic solution and the second organic solution in the cinnamaldehyde mixing solution to leave the cinnamaldehyde included partial emulsion mixture, it is only needed to use the amount of the first organic solution and the second organic solution used in the steps S110 to S130 sufficient to execute the steps S110 to S130. In detail, in step S110, it is only needed to use the amount of the first organic solution sufficient to extract cinnamaldehyde from the cinnamon leaf powder, and the ratio of the first organic solution and the cinnamon leaf powder only affects the concentration of cinnamaldehyde in the cinnamon liquid extract. In step S120, it is only needed to use the amount of the second organic solution sufficient to dissolve soybean oil, lecithin, and emulsifier.

After removing the first organic solution and the second organic solution from the cinnamaldehyde included mixing solution, the cinnamaldehyde included partial emulsion mixture would be left naturally. Thereby, when the cinnamaldehyde included partial emulsion mixture is mixed with 91 parts by weight of deionized water and then vibrate by using the ultrasonic vibrator in step S150, emulsifier in the cinnamaldehyde included partial emulsion mixture would be bonded to the water molecules effectively, so as to have the cinnamaldehyde included oil uniformly distributed in the deionized water with the help of the emulsifier to show the emulsion state. Thus, cinnamaldehyde included in the cinnamaldehyde included oil is in the condition of being dissolved in the oil and uniformly distributed in the deionized water so as to prevent aggregation of cinnamaldehyde to have cinnamaldehyde kept as individual molecules.

Although in the aforementioned embodiment, soybean oil, emulsifier, lecithin, and deionized water of the composition for inhibiting Parkinson's disease is provided at a weight ratio of 1:6:2:91 to produce cinnamaldehyde nanoemulsion, the detected composition ratio of the produced cinnamaldehyde nanoemulsion might be somewhat fluctuated. For example, take 1 part by weight of soybean oil as a reference, emulsifier might be ranged between 5 to 14 parts by weight, lecithin might be ranged between 0.5 to 2 parts by weight, and deionized water might be ranged between 81 to 91 parts by weight.

As mentioned above, based on 1 part by weight of soybean oil, after doing multigroup analysis to the compositions for inhibiting Parkinson's disease manufactured by using the aforementioned embodiment, an amount of cinnamaldehyde ranged between 2.345 to 17.833 parts by weight is detected and concentrated at the range between 8 to 12 parts by weight. Fluctuation of the amount of cinnamaldehyde is mainly due to the particle size of the cinnamon leaf powder in the beginning and the extracting process, but all the cinnamaldehyde in the composition can be nano emulsified through the aforementioned process and the reactions with other ingredients.

In addition, also based on 1 part by weight of soybean oil, after doing multigroup analysis to the compositions for inhibiting Parkinson's disease manufactured by using the aforementioned embodiment, 0.14734 to 0.8813 parts by weight of cinnamic acid, 0.04122 to 0.4334 parts by weight of cinnamyl alcohol, to 0.0833 parts by weight of kaempferol, 0.0177 to 0.0947 parts by weight of benzoic acid, 0.0102 to 0.156 parts by weight of eugenol, 0.0037 to 0.0093 parts by weight of quercetin, 0.02504 to 0.0833 parts by weight of kaempferol-3-β-D-glucopyranoside, 0.0011 to 0.0067 parts by weight of rutin, 0.00108 to parts by weight of caffeic acid, 0.00086 to 0.0012 parts by weight of coumarin, 0.00038 to 0.0014 parts by weight of hyperoside and isoquercetin, 0.00080 to 0.001 parts by weight of p-coumaric acid, and 0.00012 to 0.0015 parts by weight of neochlorogenic acid are detected. These ingredients are extracted together with cinnamaldehyde from cinnamon leaves. In practice, these minor ingredients are also contained in cinnamon leaves which have been used in the research to prove the effectiveness for inhibiting Parkinson's disease, thus, these ingredients are also helpful for inhibiting Parkinson's disease.

In order to figure out nano-scale characteristics of the cinnamaldehyde nanoemulsion, the present embodiment executes particle size distribution analysis, zeta-potential analysis, micrographic analysis, encapsulation efficiency analysis, and stability analysis for the cinnamaldehyde nanoemulsion.

Firstly, particle size distribution analysis is executed by using dynamic light scattering. When light passes through the cinnamaldehyde nanoemulsion and reaches the cinnamaldehyde particles, the light is scattered by the cinnamaldehyde particles. Because the cinnamaldehyde particles have Brownian motion in the solution, light intensity would be changed. In addition, because larger particles move slower than smaller one in the solution, particle size of cinnamaldehyde particles can be determined through the detection of light intensity change at a certain angle. Through the detection by using dynamic light scattering, the cinnamaldehyde nanoemulsion has an average particle size of 30.1 nm and a polydispersity index (PDI) of 0.149.

As mentioned above, PDI is a molecular weight distribution index, which is used to represent variation of molecular weight of polymer as an index for estimating particle size uniformity of polymer. The lower index value means particle size distribution is more uniform. General speaking, PDI value ranges between 0.1-0.3 means uniform particle size distribution, which is also indicated as narrow size distribution, PDI value over 0.5 means non-uniform particle size distribution, which is also indicated as broad size distribution. Based on the aforementioned particle size distribution analysis, it is noted that particle size of the cinnamaldehyde nanoemulsion of the present embodiment shows a single group distribution.

Furthermore, zeta-potential analysis is an important index for estimating cinnamaldehyde nanoemulsion stability. Zeta-potential is caused by the electrical charge due to dissociation, replacement, and adsorption of the groups on the particle surface. The higher zeta-potential indicates a stronger electrostatic repulsion to avoid particle aggregation, and thus represents higher stability. On the contrary, the lower zeta-potential indicates that individual particles would be aggregated easily to cause precipitation, and thus represents lower stability. Generally, 30 mV is used as the estimation value for zeta-potential, a zeta-potential value more than 30 mV or less than −30 mV indicates the solution has better stability, a zeta-potential value less than 30 mV or more than −30 mV indicates the solution has poor stability and the particles would be aggregated easily to cause precipitation. The zeta-potential value found in the cinnamaldehyde nanoemulsion of the present embodiment is −43.1 mV, which is less than −30 mV indicating that the cinnamaldehyde nanoemulsion is quite stable.

Micrographic analysis is carried out by negative staining the cinnamaldehyde nanoemulsion with phosphotungstic acid first and then observing size and types of the nano particles by using transmission electron microscope (TEM). The observation shows that the cinnamaldehyde nanoemulsion has a uniform particle size distribution, and no aggregation is found. After scale conversion, the average particle size is about 30 nm, which is similar to the average particle size of 30.1 nm detected by using dynamic light scattering.

The principle of encapsulation efficiency analysis is mentioned below. Cinnamaldehyde nanoemulsion would be layered due to polarity difference after mixing with n-Hexane and the non-encapsulated cinnamaldehyde would be suspended in the emulsion and dissolved in the n-Hexane layer after the cinnamaldehyde nanoemulsion is mixed with n-Hexane. Thus, the supernatant liquid of the n-Hexane layer can be collected for estimating free cinnamaldehyde amount (Free CIN). The encapsulation layer of the nanoemulsion would be dissolved in ethanol to release cinnamaldehyde in the nano particles, and thus the mixture can be used for estimating total cinnamaldehyde amount (Total CIN). The value of encapsulation efficiency is calculated by subtracting free cinnamaldehyde amount from total cinnamaldehyde amount, and further divided by total cinnamaldehyde amount. The cinnamaldehyde nanoemulsion of the present embodiment has an encapsulation efficiency of 91.6%.

Stability analysis is to check the change of average particle size, polydispersity index, and zeta-potential after the cinnamaldehyde nanoemulsion stored at 4° C. for 90 days, which are shown in the following table 1.

TABLE 1

| Time (days) | Average particle size (nm) | Polydispersity index | Zeta-potential (mV) |
|---|---|---|---|
| 0 | 30.1 | 0.149 ± 0.02 | −43.1 ± 0.77 |
| 7 | 32.3 | 0.175 ± 0.03 | −35.6 ± 0.70 |
| 14 | 32.1 | 0.176 ± 0.01 | −35.1 ± 1.50 |
| 21 | 30.7 | 0.168 ± 0.06 | −37.6 ± 0.71 |
| 30 | 28.9 | 0.156 ± 0.02 | −35.3 ± 0.06 |
| 60 | 27.9 | 0.148 ± 0.04 | −38.3 ± 0.68 |
| 90 | 30.5 | 0.186 ± 0.01 | −41.3 ± 1.05 |

As described in table 1, the cinnamaldehyde nanoemulsion is stored at 4° C. and sampled with certain time intervals to observe the changes of particle size and zeta-potential. The observation shows that there has no significant change regarding average particle size, polydispersity index, and zeta-potential, which indicates that cinnamaldehyde nanoemulsion stored at 4° C. has good stability.

In addition, in order to check the efficacy of the cinnamaldehyde nanoemulsion used as the composition for inhibiting Parkinson's disease, the following animal test is executed for testing the cinnamaldehyde nanoemulsion.

It is noted first that the test object of the present experiments is the mouse with Parkinson's disease induced by the insecticide rotenone. This is because it is found that rotenone may pass through blood brain barrier to damage mitochondrion system and cause the production of lipid peroxides to activate aggregation of α-synuclein, further cause DNA damage and production of Lewy body, and finally result in nervous disorder to induce Parkinson's disease.

As mentioned above, the experiments have the mice divided into the following experimental groups:

1. Normal control group (NC): mice without rotenone injection;
2. Induced group (RT): mice with injection of rotenone (2 mg/kg) for 35 days continuously;

3. High dosage cinnamon liquid extract group (EH): mice with injection of rotenone (2 mg/kg) and high dosage of cinnamon liquid extract (60 mg/kg) for 35 days continuously;
4. Low dosage cinnamon liquid extract group (EL): mice with injection of rotenone (2 mg/kg) and low dosage of cinnamon liquid extract (20 mg/kg) for 35 days continuously;
5. High dosage cinnamaldehyde nanoemulsion group (NH): mice with injection of rotenone (2 mg/kg) and high dosage of cinnamaldehyde nanoemulsion (60 mg/kg) for days continuously;
6. Low dosage cinnamaldehyde nanoemulsion group (NL): mice with injection of rotenone (2 mg/kg) and low dosage of cinnamaldehyde nanoemulsion (20 mg/kg) for days continuously; and
7. Indigenous cinnamon powder hydrosol group (HP): mice with injection of rotenone (2 mg/kg) and indigenous cinnamon powder hydrosol (10 mL/kg) for 35 days continuously.

It is noted that the dosage is calculated based on mouse weight, take the high dosage cinnamon liquid extract group (EH) for example, if mouse weight is 0.5 kg, injection dosage would be 1 mg (0.5 kg×2 mg/kg), and feeding amount of cinnamon liquid extract would be 30 mg (0.5 kg×60 mg/kg). In addition, mice of the aforementioned groups 3 to 7 are injected with rotenone first and fed with cinnamon related samples after 30 minutes.

Experiment 1: influence of cinnamon liquid extract, cinnamaldehyde nanoemulsion, and indigenous cinnamon powder hydrosol to dopamine amount in striatum of the brain of mice with Parkinson's disease induced by rotenone.

As shown in the following table 2, experiment 1 is to feed cinnamon to mice with Parkinson's disease induced by rotenone in different ways and measure dopamine amount in striatum of the brain of the mice.

TABLE 2

| Group | dopamine amount in striatum (ng/g tissue) |
|---|---|
| NC | 96.05 |
| RT | 39.72 |
| EH | 66.5 |
| EL | 47.9 |
| NH | 78.49 |
| NL | 55.46 |
| HP | 67.57 |

The result of experiment 1 indicates that, dopamine amount in striatum of the mice with Parkinson's disease induced by rotenone in the induced group (RT) is significantly lower than the normal control group (NC) with the amount of 56.33 ng/g (58.64%) ($p<0.05$). In contrast, dopamine amounts in brain of the high dosage cinnamon liquid extract group (EH), the high dosage cinnamaldehyde nanoemulsion group (NH), the low dosage cinnamaldehyde nanoemulsion group (NL), and the indigenous cinnamon powder hydrosol group (HP) are increased significantly with the amounts of 26.78 ng/g (40.27%), 38.77 ng/g (49.39%), 15.74 ng/g (28.38%) and 27.85 ng/g (41.22%), respectively. In compared with the induced group (RT), dopamine amounts in brain of the low dosage cinnamon liquid extract group (EL) is increased with the amount 8.18 ng/g (17.08%), but fails to reach significant difference ($p>0.05$). The result shows that the high dosage cinnamaldehyde nanoemulsion group (NH) has best effect for increasing dopamine (49.39%).

Experiment 2: influence of cinnamon liquid extract, cinnamaldehyde nanoemulsion, and indigenous cinnamon powder hydrosol to α-synuclein amount in striatum of the brain of mice with Parkinson's disease induced by rotenone.

As shown in the following table 3, experiment 2 is to feed cinnamon to mice with Parkinson's disease induced by rotenone in different ways and measure α-synuclein amount in striatum of the brain of the mice.

TABLE 3

| Group | α- synuclein amount (ng/g tissue) |
|---|---|
| NC | 9.58 |
| RT | 11.79 |
| EH | 9.72 |
| EL | 11.73 |
| NH | 9.91 |
| NL | 11.93 |
| HP | 11.42 |

The result of experiment 2 indicates that, α-synuclein amount in striatum of the mice with Parkinson's disease induced by rotenone in the induced group (RT) is significantly higher than the normal control group (NC) with the amount of 2.21 ng/g (18.74%) ($p<0.05$). In compared with the induced group (RT), α-synuclein amounts in brain of the high dosage cinnamon liquid extract group (EH) and the high dosage cinnamaldehyde nanoemulsion group (NH) are reduce significantly with the amounts of 2.07 ng/g (17.56%) and 1.88 ng/g (15.95%), respectively. In compared with the induced group (RT), α-synuclein amounts in striatum of the low dosage cinnamon liquid extract group (EL) and the indigenous cinnamon powder hydrosol group (HP) show the tendency of decreasing with the amount of 0.06 ng/g (0.5%) and 0.37 ng/g (3.1%), respectively, but fails to reach significant difference ($p>0.05$). In compared with the induced group (RT), α-synuclein amount in striatum of the low dosage cinnamaldehyde nanoemulsion group (NL) show no tendency of decreasing. The result shows that both the high dosage cinnamon liquid extract group (EH) and the high dosage cinnamaldehyde nanoemulsion group (NH) have best effect of reducing α-synuclein.

Experiment 3: influence of cinnamon liquid extract, cinnamaldehyde nanoemulsion, and indigenous cinnamon powder hydrosol to tyrosine hydroxylase amount in striatum of the brain of mice with Parkinson's disease induced by rotenone.

As shown in the following table 4, experiment 3 is to feed cinnamon to mice with Parkinson's disease induced by rotenone in different ways and measure tyrosine hydroxylase amount in striatum of the brain of the mice. Tyrosine hydroxylase (TH) is the enzyme for converting tyrosine to L-3,4-dihydroxyphenylalanine (L-dopa). Lack of tyrosine hydroxylase would cause the interruption of neurotransmitter and further result in shortage of dopamine, norepinephrine, etc. in central and peripheral nervous systems.

TABLE 4

| Group | Tyrosine hydroxylase (TH) amount (ng/g tissue) |
|---|---|
| NC | 325.84 |
| RT | 254.76 |
| EH | 305.36 |
| EL | 307.20 |
| NH | 342.37 |

TABLE 4-continued

| Group | Tyrosine hydroxylase (TH) amount (ng/g tissue) |
|---|---|
| NL | 324.55 |
| HP | 298.84 |

The result of experiment 3 indicates that, tyrosine hydroxylase amount in striatum of the mice with Parkinson's disease induced by rotenone in the induced group (RT) is significantly lower than the normal control group (NC) with the amount of 71.08 ng/g (21.84%) ($p<0.05$). In compared with the induced group (RT), α-synuclein amounts in striatum of the high dosage cinnamon liquid extract group (EH), the low dosage cinnamon liquid extract group (EL), the high dosage cinnamaldehyde nanoemulsion group (NH), the low dosage cinnamaldehyde nanoemulsion group (NL), and the indigenous cinnamon powder hydrosol group (HP) are increased significantly with the amounts of 50.6 ng/g (16.57%), 52.44 ng/g (17.07%), 87.61 ng/g (25.59%), 69.79 ng/g (21.5%), and 44.08 ng/g (14.75%) ($p<0.05$), respectively. The result shows that the high dosage cinnamaldehyde nanoemulsion group (NH) has the best effect.

Experiment 4: influence of cinnamon liquid extract, cinnamaldehyde nanoemulsion, and indigenous cinnamon powder hydrosol to the activity of antioxidant enzyme superoxide dismutase (SOD) in brain of the brain of mice with Parkinson's disease induced by rotenone.

As shown in the following table 5, experiment 4 is to feed cinnamon to mice with Parkinson's disease induced by rotenone in different ways and measure activity of antioxidant enzyme superoxide dismutase (SOD) in brain of the mice. Superoxide dismutase in the eukaryote would be bounded with copper ions and zinc ions to convert the superoxide anion radical into less toxic hydrogen peroxide and oxide, and acts as a first line of defense for removing free radical in body.

TABLE 5

| Group | SOD activity (U/g tissue) |
|---|---|
| NC | 387.05 |
| RT | 337.56 |
| EH | 388.01 |
| EL | 372.41 |
| NH | 405.84 |
| NL | 369.40 |
| HP | 361.75 |

The result of experiment 4 indicates that, SOD activity in brain of the mice with Parkinson's disease induced by rotenone in the induced group (RT) is significantly lower than the normal control group (NC) with the amount of 49.49 U/g (12.79%) ($p<0.05$). In compared with the induced group (RT), SOD activity in brain of the high dosage cinnamon liquid extract group (EH) and the high dosage cinnamaldehyde nanoemulsion group (NH) are increased significantly with the amounts of 50.45 U/g (13%) and 68.28 U/g (16.82%), respectively. In compared with the induced group (RT), SOD activity in brain of the low dosage cinnamon liquid extract group (EL), the low dosage cinnamaldehyde nanoemulsion group (NL) and the indigenous cinnamon powder hydrosol group (HP) show the tendency of increasing with the amount of 34.85 U/g (9.36%), 31.84 U/g (8.62%) and 24.19 U/g (6.69%), respectively, but fails to reach significant difference ($p>0.05$). The result shows that the high dosage cinnamaldehyde nanoemulsion group (NH) has best effect of increasing SOD activity (16.82%).

Experiment 5: influence of cinnamon liquid extract, cinnamaldehyde nanoemulsion, and indigenous cinnamon powder hydrosol to the activity of malondialdehyde (MDA) in brain of the brain of mice with Parkinson's disease induced by rotenone.

As shown in the following table 6, experiment 5 is to feed cinnamon to mice with Parkinson's disease induced by rotenone in different ways and measure activity of malondialdehyde in brain of the mice. Malondialdehyde (MDA) is an index of lipid peroxidation and is peroxidation products of free radicals and fatty acids.

TABLE 6

| Group | Malondialdehyde (MDA) amount (nmol/min/g tissue) |
|---|---|
| NC | 375.25 |
| RT | 456.70 |
| EH | 386.07 |
| EL | 374.57 |
| NH | 354.10 |
| NL | 363.66 |
| HP | 382.74 |

The result of experiment 5 indicates that, MDA activity in brain of the mice with Parkinson's disease induced by rotenone in the induced group (RT) is significantly higher than the normal control group (NC) with the amount of 81.45 nmol/min/g (17.83%) ($p<0.05$). In compared with the induced group (RT), MDA activity in brain of the high dosage cinnamon liquid extract group (EH), the low dosage cinnamon liquid extract group (EL), the high dosage cinnamaldehyde nanoemulsion group (NH), the low dosage cinnamaldehyde nanoemulsion group (NL), and the indigenous cinnamon powder hydrosol group (HP) are reduced significantly with the amounts of 70.63 nmol/min/g (15.47%), 82.13 nmol/min/g (17.98%), 102.6 nmol/min/g (22.47%), 93.04 nmol/min/g (20.37%), and 73.97 nmol/min/g (16.19%) ($p<0.05$), respectively, and wherein the high dosage cinnamaldehyde nanoemulsion group has the greatest reduction (22.47%).

Experiment 6: behavioral test of mice with Parkinson's disease induced by rotenone fed with cinnamon liquid extract, cinnamaldehyde nanoemulsion, and indigenous cinnamon powder hydrosol.

As shown in the following table 7, experiment 6 is to feed cinnamon to mice with Parkinson's disease induced by rotenone in different ways and do the behavioral test for the mice. Parkinson's disease is a neurodegenerative disease, featuring the damage of neurons in substantia nigra pars compacta, which may cause movement disorders together with tremor, rigid muscle, and reduced balance. Freezing test is for detecting muscle rigidity of mice.

TABLE 7

| Group | Freezing time (sec) |
|---|---|
| NC | 2 |
| RT | 26 |
| EH | 13 |
| EL | 22 |
| NH | 10 |
| NL | 16 |
| HP | 21 |

The result of experiment 6 indicates that, freezing time of the mice with Parkinson's disease induced by rotenone in the induced group (RT) is significantly longer than the normal control group (NC) with the amount of 24 seconds (92.31%) ($p<0.05$). In compared with the induced group (RT), freezing time of the high dosage cinnamon liquid extract group (EH), the low dosage cinnamon liquid extract group (EL), the high dosage cinnamaldehyde nanoemulsion group (NH), the low dosage cinnamaldehyde nanoemulsion group (NL), and the indigenous cinnamon powder hydrosol group (HP) is reduced significantly with the amounts of 13 seconds (50.00%), 4 seconds (15.38%), 16 seconds (61.54%), 10 seconds (38.46%), and 5 seconds (19.23%) ($p<0.05$), respectively, and wherein the high dosage cinnamaldehyde nanoemulsion group has the greatest reduction of freezing time (61.54%).

According to the above mentioned experiments 1 to 6, it is found that cinnamaldehyde nanoemulsion is more effective than the existed cinnamon liquid extract or indigenous cinnamon powder hydrosol for inhibiting Parkinson's disease, and thus the cinnamaldehyde nanoemulsion produced by using the method of manufacturing composition for inhibiting Parkinson's disease in accordance with the present invention can be actually used as the composition for inhibiting Parkinson's disease.

The foregoing descriptions are merely preferred embodiments of this disclosure, and do not constitute any limitation on this disclosure. Any form of variation such as equivalent replacement or modification made to the technical means and technical content disclosed in this disclosure without departing from the scope of the technical means of this disclosure is the content of the technical means of this disclosure and still falls within the protection scope of this disclosure.

What is claimed is:

1. A composition for inhibiting Parkinson's disease comprising 1 part by weight of soybean oil, 5 to 14 parts by weight of emulsifier, 0.5 to 2 parts by weight of lecithin, 81 to 91 parts by weight of deionized water, and 2.345 to 17.833 parts by weight of cinnamaldehyde, wherein an average particle size of the composition for inhibiting Parkinson's disease is 30 nm, and a polydispersity index of the composition for inhibiting Parkinson's disease is ranged between 0.14 to 0.18.

2. The composition for inhibiting Parkinson's disease of claim 1, further comprising 0.14734 to 0.8813 parts by weight of cinnamic acid.

3. The composition for inhibiting Parkinson's disease of claim 1, further comprising 0.04122 to 0.4334 parts by weight of cinnamyl alcohol.

4. The composition for inhibiting Parkinson's disease of claim 1, further comprising 0.02504 to 0.0833 parts by weight of kaempferol.

5. The composition for inhibiting Parkinson's disease of claim 1, further comprising 0.0177 to 0.0947 parts by weight of benzoic acid.

6. The composition for inhibiting Parkinson's disease of claim 1, further comprising 0.0102 to 0.156 parts by weight of eugenol.

7. The composition for inhibiting Parkinson's disease of claim 1, further comprising 0.0037 to 0.0093 parts by weight of quercetin.

8. The composition for inhibiting Parkinson's disease of claim 1, further comprising 0.02504 to 0.0833 parts by weight of kaempferol-3-β-D-glucopyranoside.

9. The composition for inhibiting Parkinson's disease of claim 1, further comprising 0.0011 to 0.0067 parts by weight of rutin.

10. The composition for inhibiting Parkinson's disease of claim 1, further comprising 0.00108 to 0.00521 parts by weight of caffeic acid, 0.00086 to 0.0012 parts by weight of coumarin, 0.00038 to 0.0014 parts by weight of hyperoside and isoquercetin, 0.00080 to 0.001 parts by weight of p-coumaric acid, and 0.00012 to parts by weight of neochlorogenic acid.

11. A method of manufacturing the composition for inhibiting Parkinson's disease of claim 1, comprising the steps of:

(A) preparing a cinnamon liquid extract, wherein the cinnamon liquid extract comprises a first organic solution and at least one solute totally dissolved in the first organic solution, wherein the at least one solute comprises 90% to 99% by weight of cinnamaldehyde;

(B) having 1 part by weight of soybean oil, 2 parts by weight of lecithin, and 6 parts by weight of emulsifier dissolved in a second organic solution as an emulsifier mixing solution, wherein the first organic solution and the second organic solution are ethanol solutions;

(C) adding 200 parts by weight of the cinnamon liquid extract in the emulsifier mixing solution and mixing to form a cinnamaldehyde included mixing solution, wherein the cinnamaldehyde included mixing solution comprises the first organic solution and the second organic solution, wherein the cinnamaldehyde, the soybean oil, and the lecithin in the cinnamaldehyde add mixing solution are miscible with each other to form a cinnamaldehyde included oil, and the cinnamaldehyde included oil and the emulsifier are partially bonded to form a cinnamaldehyde included partial emulsion mixture;

(D) executing a drying process to remove the first organic solution and the second organic solution in the cinnamaldehyde mixing solution to leave the cinnamaldehyde included partial emulsion mixture; and (E) mixing the cinnamaldehyde included partial emulsion mixture with 91 parts by weight of deionized water to form a cinnamaldehyde nanoemulsion as the composition for inhibiting Parkinson's disease.

12. The method of claim 11, wherein the step (E) is to mix the cinnamaldehyde included partial emulsion mixture with 91 parts by weight of the deionized water and then vibrate by using an ultrasonic vibrator to form the cinnamaldehyde nanoemulsion.

13. The method of claim 11, wherein a concentration of the ethanol solution is higher than 80%.

14. The method of claim 11, wherein the step (A) is to extract cinnamon leaf powder with the first organic solution to prepare the cinnamon liquid extract.

15. The method of claim 14, wherein a weight ratio of the cinnamon leaf powder and the first organic solution is 1:5.

* * * * *